US00PP10810P

United States Patent [19]

Toews

[11] Patent Number: Plant 10,810

[45] Date of Patent: Mar. 2, 1999

[54] PEACH TREE NAMED 'SIERRA GEM'

[75] Inventor: Ron Toews, Reedley, Calif.

[73] Assignee: The Burchell Nursery, Inc., Oakdale, Calif.

[21] Appl. No.: 923,066

[22] Filed: Sep. 3, 1997

[51] Int. Cl.[6] ..... A01H 5/00

[52] U.S. Cl. ..... Plt./43.2

[58] Field of Search ..... Plt./43.2, 42.1, Plt./43.1

*Primary Examiner*—Howard J. Locker

*Attorney, Agent, or Firm*—Wells, St. John, Roberts, Gregory & Matkin, P.S.

[57] ABSTRACT

A new and distinctive variety of peach tree is described and which is a chance sport of a 'Fancy Lady' peach tree (U.S. Plant Pat. No. 7,023), but which is distinguishable therefrom and, characterized principally as to novelty by producing fruit which are ripe for harvesting and shipment some seven days earlier than 'Fancy Lady' peach tree at the same geographical location.

1 Drawing Sheet

BACKGROUND OF THE NEW VARIETY

The present invention relates to a new and distinct variety of peach tree which will hereinafter be denominated varietarily as 'Sierra Gem', and more particularly to a peach tree which produces fruit which are ripe for commercial harvesting and shipment between about June 12 to about June 16 under the environmental conditions prevailing in the San Joaquin Valley of Central California. The present variety is further distinguished as to novelty by producing a freestone fruit which has a noteworthy flavor in comparison to the commercial varieties which mature in the same season, and which additionally has a higher degree of coloration and a distinctive yellow-orange stripe which occurs along or in the suture. The present variety of peach tree is mature for harvesting and shipment approximately one week before its parent, 'Fancy Lady', (U.S. Plant Pat. No. 7,023).

Although there is a number of criteria which a commercial variety of tree fruit must meet or exceed if it is to be successful in the fresh market, without question, the ripening date, flavor, coloration of the skin, texture, shipping quality and size are among the most important factors. For example, an attractive color as well as good to excellent flavor, if particularly distinctive and different than currently existing varieties attracts immediate attention in the marketplace. These characteristics, among others, enhance the likelihood that the variety will be a commercial success.

It should be understood that fresh market peaches are characterized by two separate color types, that is, white-fleshed peaches and yellow fleshed peaches. In the case of white fleshed peaches, this variety is characterized by a ground color which is lighter than the yellow-fleshed varieties. In addition, the intensity of the blush color and quantity of same is normally greater on the yellow-fleshed varieties. Additionally, the yellow-fleshed peach varieties, in contrast, are typically characterized by a yellow to orange skin coloration with a red blush of various degrees.

ORIGIN AND ASEXUAL REPRODUCTION OF THE NEW VARIETY

The present variety of peach tree was discovered by the inventor within the cultivated area of his peach orchard which is located approximately 1¾ miles south of Manning Avenue on the east side of Lac Jac Road in Reedley, Calif., during the growing season of 1991. The present variety was discovered growing as a chance sport in a planting of 'Fancy Lady' peach trees (U.S. Plant Pat. No. 7,023). The inventor, at that time, noted its unique characteristics and marked the subject sport for subsequent observation. The inventor has observed the sport for the last five years. Subsequent to discovery, the inventor removed scion wood from the marked sport and grafted it into Nemagard seedlings during the 1991 and 1992 season. These test trees were located in another peach planting owned by the inventor, and which is located on the north side of Huntsman Avenue, and approximately ½ mile east of Lac Jac Road in Reedley, Calif. Continued observation of the original sport and the asexually reproduced progeny has confirmed that the distinguishing characteristics of the plant run true to the original sport and are faithfully transmitted through such asexual propagation.

SUMMARY OF THE NEW VARIETY

The 'Sierra Gem' peach tree is characterized as to novelty by producing a freestone fruit which has an attractive orange to reddish blush, and a noteworthy yellow skin coloration with a distinctively attractive yellow-orange stripe in the suture region. Further, the fruit produced by the 'Sierra Gem' peach tree is ripe for commercial harvesting and shipment approximately June 12 to June 16 under the environmental conditions existing in the San Joaquin Valley of Central California. The new and novel variety of peach tree is perhaps most closely similar to its parent 'Fancy Lady', (U.S. Plant Pat. No. 7,023), but is distinguishable therefrom and characterized principally as to novelty by producing a high quality, fresh market, freestone, yellow fleshed peach of medium size and which ripens during the second week of June and which additionally possesses a high degree of color with a distinctive yellow-orange stripe in the suture region. In further contrast with the fruit of the 'Fancy Lady' peach tree, (U.S. Plant Pat. No. 7,023), the new variety produces fruit which are equal to or slightly larger in size than that produced by 'Fancy Lady' peach tree and has a considerably richer flavor than the fruit produced by the 'Fancy Lady' peach tree.

In addition to the foregoing, the exterior appearance of the new variety and the parent 'Fancy Lady' vary substantially. For example, the exterior appearance of the fruit produced by the 'Fancy Lady' peach tree is characteristic of most yellow-freestone peach varieties grown in California, that is, it has a mostly orange skin coloration and occasionally, some amount of reddish blush may appear on the skin of the fruit which has been exposed to direct sunlight. In contrast, the new variety of peach has increased amounts of red coloration (blush). Still further, the new variety has, as earlier noted, a distinctive yellow- orange color in the suture.

BRIEF DESCRIPTION OF THE DRAWING

The accompanying drawing is a color photograph of a characteristic twig bearing typical leaves, several of which display both the dorsal and ventral coloration thereof, and mature fruit showing both their internal and external coloration sufficiently matured for harvesting and shipment. Additionally, one fruit is dissected in the axial plane to illustrate the stone characteristics thereof. All of the fruit are of the subject variety.

All color code designations are by reference to the Dictionary of Color, by Maerz and Paul, First Edition 1930. Common color names are also employed occasionally.

Tree:

*Vigor.*—Vigorous.

*Chilling requirements.*—Normal for peach trees grown under typical San Joaquin Valley climatic conditions.

*Figure.*—Upright, spreading and open in density with the eventual shape and form determined by pruning practices.

*Productivity.*—Productive.

*Regularly of bearing.*—Regular.

Trunk:

*Size.*—Large in diameter in relative comparison to other peach cultivars.

*Surface texture.*—Moderately smooth with some rough areas.

Color:

*Old bark.*—Page 132, Plate 55, A-3, Pigeon.

*Less mature bark.*—Scaffold branches which are somewhat smoother appear more brown colored — Plate 55, C-3.

*Lenticels.*—Numbers — numerous. Size — medium.

Branches:

*Size.*—Medium as compared to other varieties.

*Surface texture.*—Considered smooth.

*Color.*—One year or older wood — page 38, plate 8, E6, Rose Ebony. Immature branches — page 62, plate 20, J 3, Shadow Green.

*Surface texture.*—Immature growth — considered smooth.

Leaves:

*Size.*—Average length — approximately 147–166 mm (5.79 to 6.54 inches). Average width — approximately 37–47 mm (1.46 to 1.85 inches). Thickness — about average.

*Form.*—Shape — Lanceolate. Leaf tip — Acute to acuminate.

*Color.*—Upwardly disposed surface — Page 68, Plate 23, J8, Mt. Vernon Green. Downwardly disposed surface — Page 66, Plate 22, I3.

*Leaf vein.*—Midvein on lower leaf surface — Page 60, Plate 19, 5B, Nile Green.

*Leaf margin.*—Slightly undulating; and generally finely serrate or crenate.

*Glands.*—Reniform — small in size; generally 3–4 per leaf; an located on both sides of leaf; color — green. This color is not particularly distinctive, however.

*Petiole.*—Length — approximately 11–14 mm (0.43 to 0.55 inches). Width — approximaetly 1.5 mm (0.059 inch). Color — Page 64, Plate 21, 2L, Moss Green.

*Stipules.*—None are apparent.

Flowers:

*Buds.*—Shape — they assume the shape of a simple bud. Width — approximately 7–9 mm (0.28 to 0.35 inches). Length — approximately 10–12 mm (0.39 to 0.47 inches). Surface texture — slightly pubescent.

*Date of first bloom.*—Feb. 25, 1997, under environmental conditions prevailing in the San Joaquin Valley of central California.

*Date of full bloom.*—Mar. 6, 1997, under the environmental conditions prevailing in the San Joaquin Valley of central California.

*Bloom size.*—approximately 16–18 mm (0.63–0.71 inches) in diameter.

*Petals—Color — peripheral edge — Page* 128, Plate 53, 9B. Color — central portion — Page 128, Plate 53, C5.

*Stamens.*—About 25–30 per bloom.

Fruit:

*Maturity when described.*—Ripe for commercial harvesting and shipping approximately Jun. 12–16, 1997, at Reedley, Calif. in the San Joaquin Valley of central California. The yellow-fleshed freestone fruit matures about sevn days earlier than that of the 'Fancy Lady' peach tree (U.S. Plant Pat. No. 7,023) in the Reedley area, and is slightly larger in size.

*Size.*—Average diameter in the suture plane — approximately 65 mm (2.56 inches). Average diameter transverse to the suture plane — approximately 70 mm (2.76 inches). Average diameter transverse and at right angle to the suture plane — approximately 70 mm (2.76 inches).

*Form.*—Uniformity — fairly uniform. Symmetry — symmetrical and considered globose.

*Ripening.*—Even.

*Suture.*—Moderately pronounced but shallow.

*Ventral surface.*—Generally slightly rounded at the base.

*Stem cavity.*—Obtuse. Length — approximately 25–35 mm (0.98 to 1.38 inches). Width — approximately 20–25 mm (0.79 to 0.98 inches). Depth — approximately 18–19 mm (0.71 to 0.75 inches).

*Stem.*—Length — approximately 8 mm (0.31 inches). Width — approximately 5 mm (0.20 inches).

*Pistil point.*—Form — considered shallow; slightly pointed.

*Skin.*—Down — moderate. Tendency to crack — not known. Blush coloration — Page 32, Plate 5, L8, Barberry Ground coloration — Page 32, Plate 5, L10, Chimney R+.

*Flesh.*—Color — Page 46, Plate 12, J5, Light Stone. Texture — medium. Flavor — excellent and considered subacid. Aroma — Pleasant and considered very good. Juice — very good. Surface texture of pit cavity — rough. Color of pit cavity — Page 46, Plate 12,J5. Color of pit well — Page 46, Plate 12, L6, Punjab. Fibers — Numerous; approximately 15–25 mm in length (0.89 to 0.98 inches).

*Stone.*—Attachment — freestone. Size — Length — approximately 25–31 mm (0.98 to 1.46 inches). Width — approximately 20–25 mm (0.79 to 0.98 inches). Thickness — approximately 17–19 mm (0.67 to 0.75 inches). Form — generally oval to oblong. Color — Page 50, Plate 14, 8B, Tanbark Algerian. Sides — equal in size and deeply pitted near the base. Ridges — several on each side, located near the apex and base. Base — shape is rounded. Size and position of grooves — deep and near the apex. Dorsal edge — thin, with deep grooves throughout. Ventral edge — thin, with a wing present throughout. Splitting tendency — not evident.

*Use.*—fresh market.

*Eating quality.*—Very good.

*Keeping quality.*—Good.

*Shipping quality.*—Good.

Although this new variety of peach tree possesses the above described characteristics as a result of the growing conditions prevailing near Reedley, Calif., in the San Joaquin Valley of central California, it is to be understood that variations of the usual magnitude and characteristics incidental to changes in growing conditions and cultural practices are to be expected.

Having thus described and illustrated my new variety of peach tree, which I claim as new and desire to be secured by Plant Letters Patent is:

1. A new and distinctive variety of peach tree substantially as illustrated and described and which is characterized as to novely by producing a yellow, freestone fruit which is mature for commerical harvesting and shipment approximately Jun. 12–16 under the environmental conditions prevailing in the San Joaquin Valley of Central California, and which fruit further has a distinctive surface color and a pleasing flavor.

* * * * *

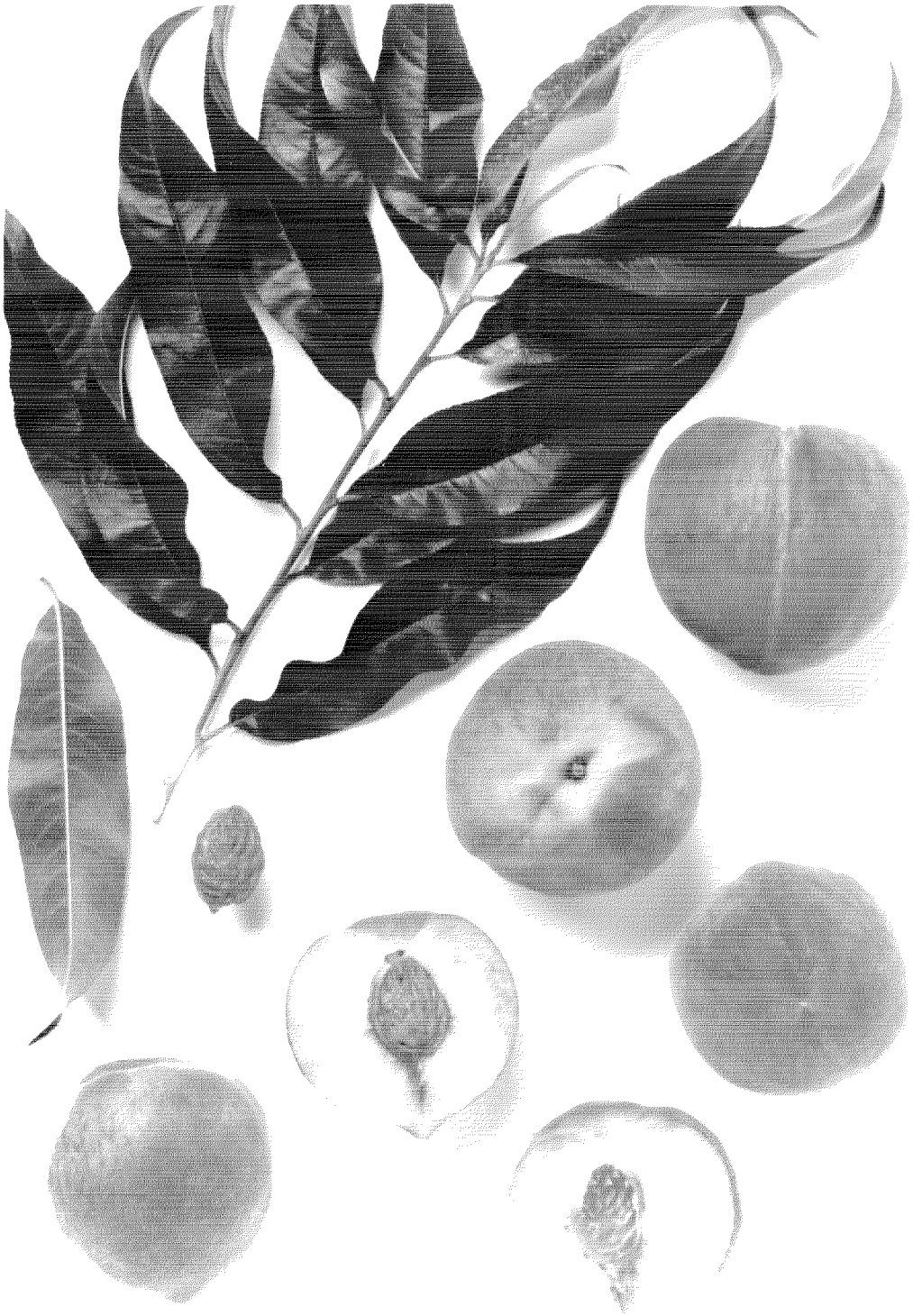

UNITED STATES PATENT AND TRADEMARK OFFICE

CERTIFICATE OF CORRECTION

PATENT NO. : PP10,810
DATED : March 2, 1999
INVENTOR(S) : Ron Toews

It is certified that error appears in the above-identified patent and that said Letters Patent is hereby corrected as shown below:

In column 3, line 64, delete the word "an" and insert the word --and--

In column 4, line 26, delete the word "sevn" and insert the word --seven--

In column 6, line 9, delete the word "novely" and insert the word --novelty--

Signed and Sealed this

Fourth Day of April, 2000

*Attest:*

*Attesting Officer*

Q. TODD DICKINSON

*Director of Patents and Trademarks*